(12) United States Patent
Pang

(10) Patent No.: US 8,388,576 B2
(45) Date of Patent: Mar. 5, 2013

(54) DILATOR AND A METHOD OF MANUFACTURING THE SAME

(76) Inventor: Ah San Pang, Singapore (SG)

( * ) Notice: Subject to any disclaimer, the term of this patent is extended or adjusted under 35 U.S.C. 154(b) by 0 days.

(21) Appl. No.: 12/992,172

(22) PCT Filed: May 29, 2008

(86) PCT No.: PCT/SG2008/000195
§ 371 (c)(1),
(2), (4) Date: Feb. 24, 2011

(87) PCT Pub. No.: WO2009/145728
PCT Pub. Date: Dec. 3, 2009

(65) Prior Publication Data
US 2011/0144580 A1   Jun. 16, 2011

(51) Int. Cl.
*A61M 29/00* (2006.01)
(52) U.S. Cl. ........................................... 604/104
(58) Field of Classification Search .................. 604/104, 604/174, 175, 96.01
See application file for complete search history.

(56) References Cited

U.S. PATENT DOCUMENTS

| | | | |
|---|---|---|---|
| 5,084,014 A * | 1/1992 | Picha et al. | ............... 604/500 |
| 5,356,382 A | 10/1994 | Picha et al. | |
| 5,555,898 A | 9/1996 | Suzuki et al. | |
| 2007/0016172 A1 | 1/2007 | Charukhchian | |
| 2007/0142780 A1 * | 6/2007 | Van Lue | ............... 604/167.01 |

FOREIGN PATENT DOCUMENTS

WO  WO 2007/027920  3/2007

OTHER PUBLICATIONS

International Search Report dated Sep. 4, 2008.
International Preliminary Report on Patentability dated Sep. 23, 2008.

* cited by examiner

*Primary Examiner* — Aarti B Berdichevsky
(74) *Attorney, Agent, or Firm* — VLP Law Group LLP; Enshan Hong; Kent H. Cheng

(57) ABSTRACT

A Dilator and a method of manufacturing the same A medical dilator for a gastrostomy feeding tube comprising a first portion (12) a second portion (38) and a central filament (34) having a first end and a second end wherein the first end of the central filament (34) is connected to the first portion (12) and the second end of the central filament (34) is connected to the second portion (38) such that the first and second portion are able to couple together to form an assembled dilator and the central filament is able to fold to form a pull loop. A method of manufacturing the dilator, a tube adapted to be engaged by the dilator and a kit comprising the same.

14 Claims, 6 Drawing Sheets

1A

1B

1C

1D

1E

DILATOR AND A METHOD OF MANUFACTURING THE SAME

PRIORITY CLAIM

This is a U.S. national stage of application No. PCT/SG2008/000195, filed on May 29, 2008, the content of which is incorporated here by reference.

FIELD OF THE INVENTION

The present invention generally relates to gastrostomy. In particular the invention relates to a dilator for use in percutaneous endoscopic gastrostomy and its method of manufacture.

BACKGROUND ART

In a patient who is unable to feed in the normal way via the mouth, a feeding tube is frequently used by doctors to convey nutrition directly to the stomach. When the tube enters the stomach through an aperture in the abdomen, it is called a gastrostomy feeding tube. The preferred technique to insert the tube in gastrostomy operations is the pull-method of percutaneous endoscopic gastrostomy (PEG pull-method).

In the PEG pull-method, a conical dilator with a wire loop at its tip is pulled through the tissues, creating a tunnel for the tube to pass.

Many steps are needed to manufacture the dilator as illustrated in FIG. 1. The first step is the crimping of a length of wire to form the loop at one end and two blunt ends at the other (FIG. 1A). Next, the body of the dilator is insert-molded around a portion of the crimped wire such that the crimped wire loop protrudes from the tip of the dilator and the blunt ends of the crimped wire protrude from the base of the dilator (FIG. 1C). This base is the portion of the dilator that is pushed into one end of the feeding tube. The base of the dilator is ribbed (or barbed) so that the dilator and tube do not separate easily. The third step involves trimming the ends of the blunt ends of the crimped wire protruding from the base of the dilator so they are more or less flush with the base (not shown).

The tube is then fitted over the base of the dilator until the edge of the tube is flush with the largest diameter of the conical portion of the dilator (FIG. 1D). If there is a gap, there is a risk of the end of the tube snagging on tissues. To make the joint more secure, a liquid adhesive is often injected to bond the tube and the dilator together as the final step (FIG. 1E). Alternatively, a sheath of specialty plastic is heat-shrunk over the joint. The manufacture of such a dilator is time consuming, labour intensive and expensive. Such dilators may also be difficult to assemble and use.

The preceding discussion of the background to the invention is intended only to facilitate an understanding of the present invention. It should be appreciated that the discussion is not an acknowledgment or admission that any of the material referred to was part of the common general knowledge as at the priority date of the application.

It is an object of this invention to provide a dilator and a method of manufacturing the same that ameliorates the problems of prior art dilators and current methods of manufacturing the same.

SUMMARY OF INVENTION

Throughout this document, unless otherwise indicated to the contrary, the terms "comprising", "consisting of", and the like, are to be construed as non-exhaustive, or in other words, as meaning "including, but not limited to".

In accordance with a first aspect of the present invention there is provided a medical dilator for a gastrostomy feeding tube comprising a first portion a second portion, and a central filament having a first end and a second end wherein the first end of the central filament is connected to the first portion and the second end of the central filament is connected to the second portion such that when the first and second portion are coupled together to form an assembled dilator, the central filament folds back on itself to form a pull loop.

The resulting dilator may be provided preassembled or ready to assemble making the dilator easy to assemble and use by any medical personnel.

Preferably the dilator may consist of a polymer that has sufficient rigidity to open a stoma, yet flexible enough to allow the dilator to be bent through a patient.

Preferably the first portion of the dilator further comprises two or more projections interspaced with a recess between the projections and the second portion of the dilator comprises one or more projection between recesses such that, when the first and second portions are coupled, the projections on the first portion are received within the recesses of the second portion and vice-versa, the alternating arrangement interlocking to secure the coupling.

Preferably the dilator has a base and a top, the top being the portion from which the central filament extends to form the pull loop, the assembled dilator may further comprise an at least one protrusion extending from the base to engage the end of the tube. The connection may be achieved over the end of the tube adapted to be engaged by the at least one protrusion from the first or second half wherein the at least one securely engages the end of the tube.

In one embodiment preferably the dilator may further comprise a first and second lip that forms a sheath when the dilator is assembled the sheath adapted to envelope the end of the tube.

In another embodiment preferably the dilator may further comprise a first flange protruding from the first portion and a second flange protruding from the second portion, the first and second portion arranged to form a plug adapted to firmly engage the tube when the dilator is assembled. Preferably the plug comprises barbs to securely grip the internal diameter of the tube.

Preferably the dilator may further comprise a hollow piece adapted to surround the assembled dilator. The hollow piece may be cylindrical or frusto-conical.

In accordance with another aspect of the present invention there is provided a tube adapted to be engaged by the dilator of the first aspect of the invention.

Preferably the tube has an indent at an end thereof for facilitating connection of the tube to the dilator.

Preferably the tube has an aperture at the end at the end thereof for receiving a protrusion of the dilator when the dilator is connected to that end of the tube.

In accordance with another aspect of the present invention there is provided a kit comprising a dilator of the invention and a tube adapted to be engaged by the dilator.

The kit may include the dilator in its assembled form. The dilator may be assembled and connected to the tube adapted to be engaged by the dilator.

In accordance with another aspect of the present invention there is provided a method of manufacturing a medical dilator for a gastrostomy feeding tube comprising the step of casting a dilator in a mold in the inverse of the dilator, the mold operable to define a first cast space for a first portion of the dilator, a second cast space for a second portion of the dilator and a third cast space for a central filament.

Preferably the dilator may be manufactured as single structure which may require only one material; furthermore, it may be manufactured in a single step using a molding technique. The casting may be via injection molding or other known molding techniques.

In accordance with another aspect of the present invention there is provided a method of assembling a medical dilator comprising a first portion and a second portion connected by way of a central filament, the method comprising the step of interlocking the first portion of the dilator with the second portion of the dilator such that the central filament folds back on itself to form a pull loop.

The method may further comprise the step of attaching a protrusion extending from the first or second portion to a tube such that the tube is connected to the dilator at a position substantially opposite that of the pull loop. The method may further comprise the step of connecting the assembled dilator to the end of the tube.

The dilator is easy to manufacture. The dilator may be manufactured in just one to a few simple steps. Similarly the dilator may be easy to assemble by almost anyone.

BRIEF DESCRIPTION OF THE DRAWINGS

The invention will be better understood by reference to the following drawings in which.

DETAILED DESCRIPTION OF THE PREFERRED EMBODIMENTS OF THE INVENTION

Figure 1:
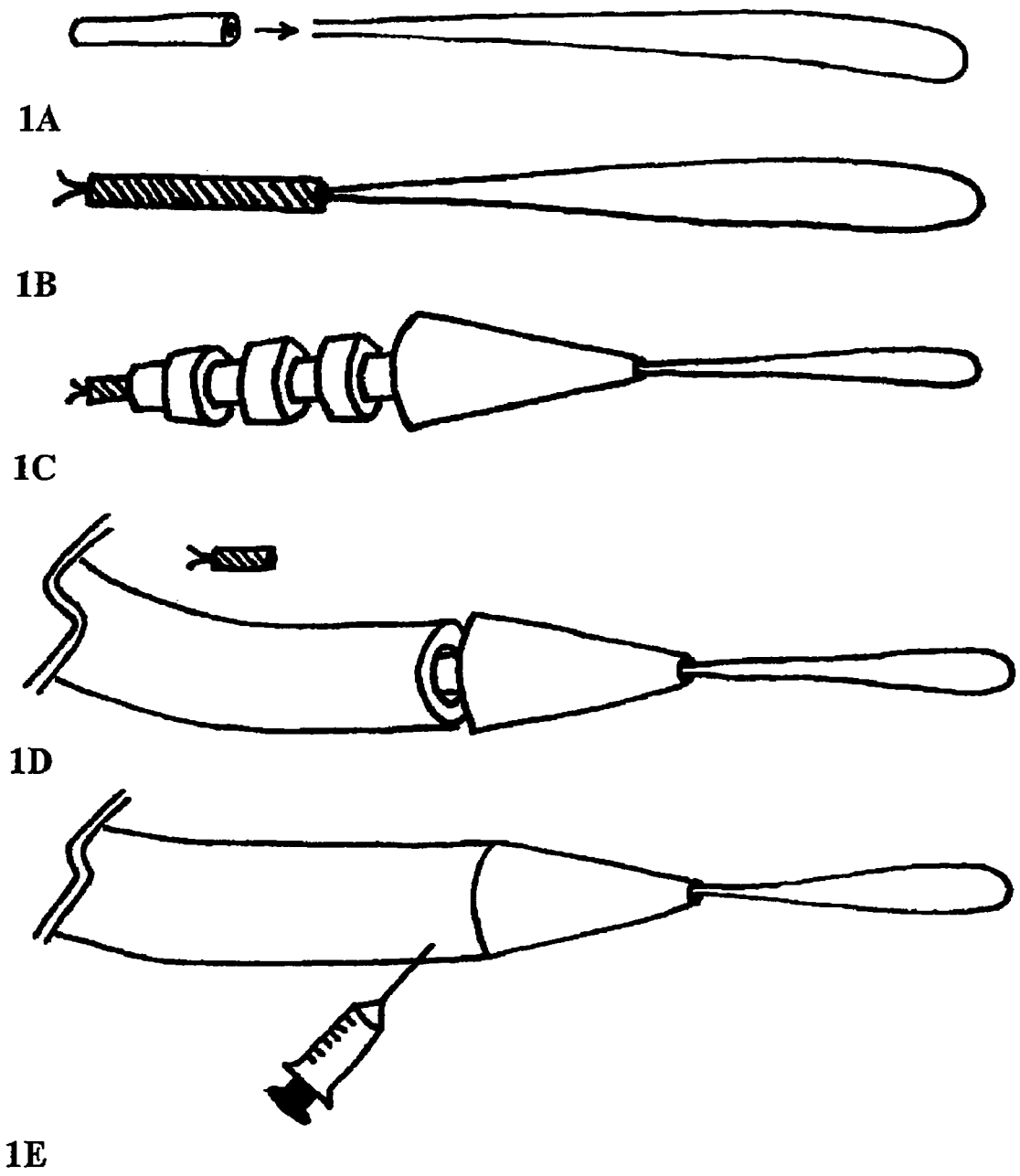
FIG. 1 is an illustration of the steps involved in the manufacture of a prior art dilator with pull loop.
Figure 2:
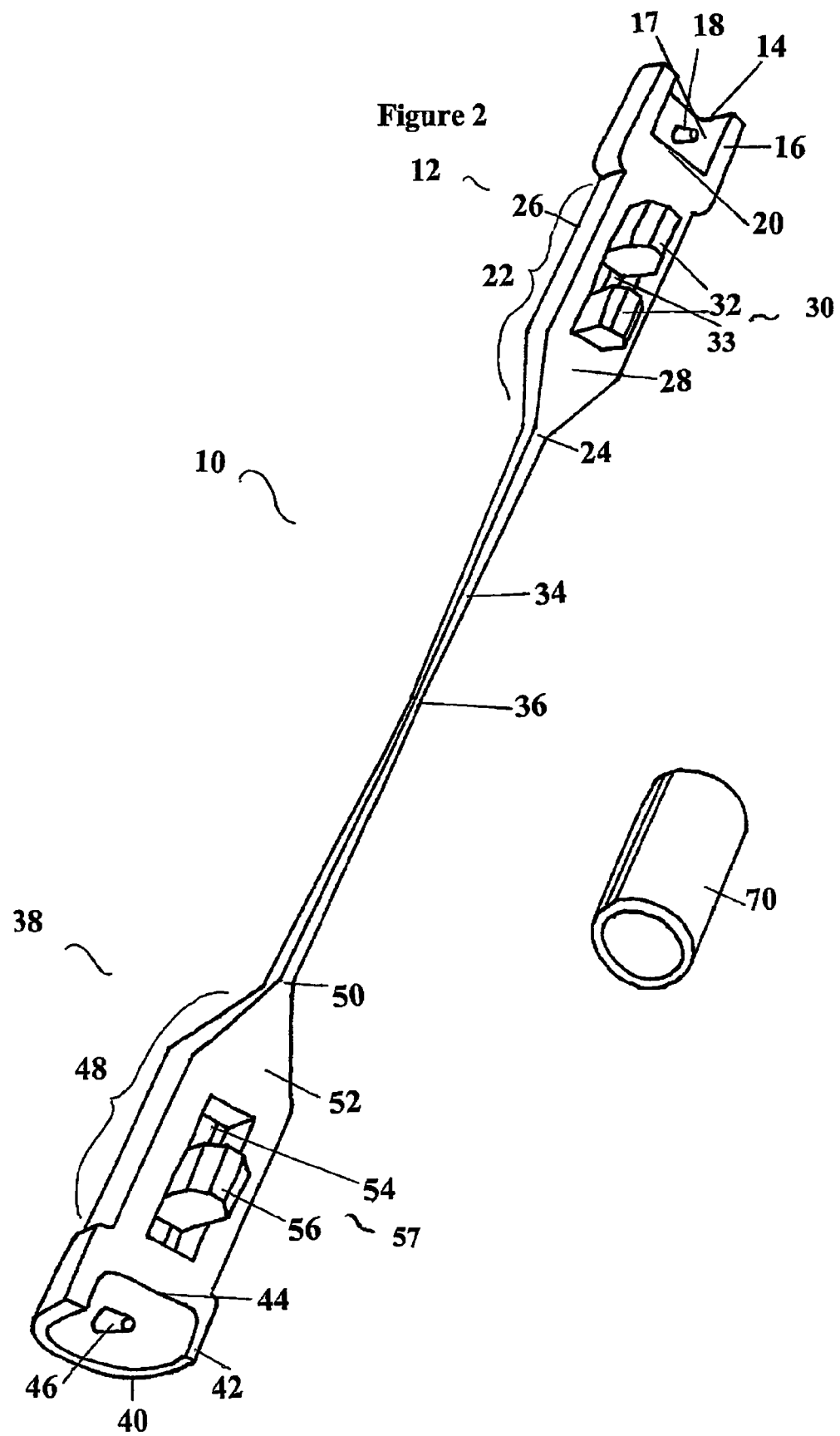
FIG. 2 is an illustration of a dilator before assembly according to a first embodiment of the invention.

Referring to FIG. 2 in accordance with a first embodiment a dilator 10 comprises a first portion 12. The first portion having a first end 14 with a lip 16. The lip 16 surrounds a substantially semi-circular recess area 17. Moving from the first end along the recess area 17 towards a base portion 20 a cavity is formed having an inner wall defining the cavity. Within the cavity on the inner wall of the lip 16 a protrusion 18 is formed.

Abutting the base portion 20 is a main portion 22. The main portion 22 is elongate and tapers gradually to a narrow point 24 from the end portion 20. The side of the main portion continuing from the open face of the cavity has a predominantly flat outer segment 28 surrounding an inner segment 30 comprising two projections 32 interspaced with a recess 33 between the projections forming a well within the main portion 22. The predominantly flat outer segment 28 extends around the other side of the main portion 22 curved to form a shape 26 approximating that of a conical shape that has been sliced longitudinally.

The first embodiment further comprises a central filament 34 connected to the first portion 12 at the narrow point 24. The central filament 34 is about the same thickness as the narrow point 24. The central filament extends and is connected to a second portion 38. The central filament 34 narrows at a central point 36. The central filament 34 elongates from the two portions and tapers slightly towards a central point 36. A second half of the central filament 34 is connected to the second portion 38 at a second narrow point 50 of a second main portion 48.

The second portion 38 is formed in a similar shape to that of the first portion 12 described above having a second end 40 with a second lip 42 forming a second cavity wherein an inner wall defining the cavity has a second base portion 44. Within the cavity on the inner wall of the second lip 42 a second protrusion 46 is formed.

Abutting the second base portion 44 of the second lip 42 is a second main portion 48. The second main portion 48 is formed in a similar shape to the main portion 22 described above having a second narrow point 50 and a predominantly flat outer segment 52 surrounding an inner segment 54. The inner segment 57 has a central projection 56 with a recess 54 either side of the central projection 56 forming two wells within the second main portion 48.

Figure 5:
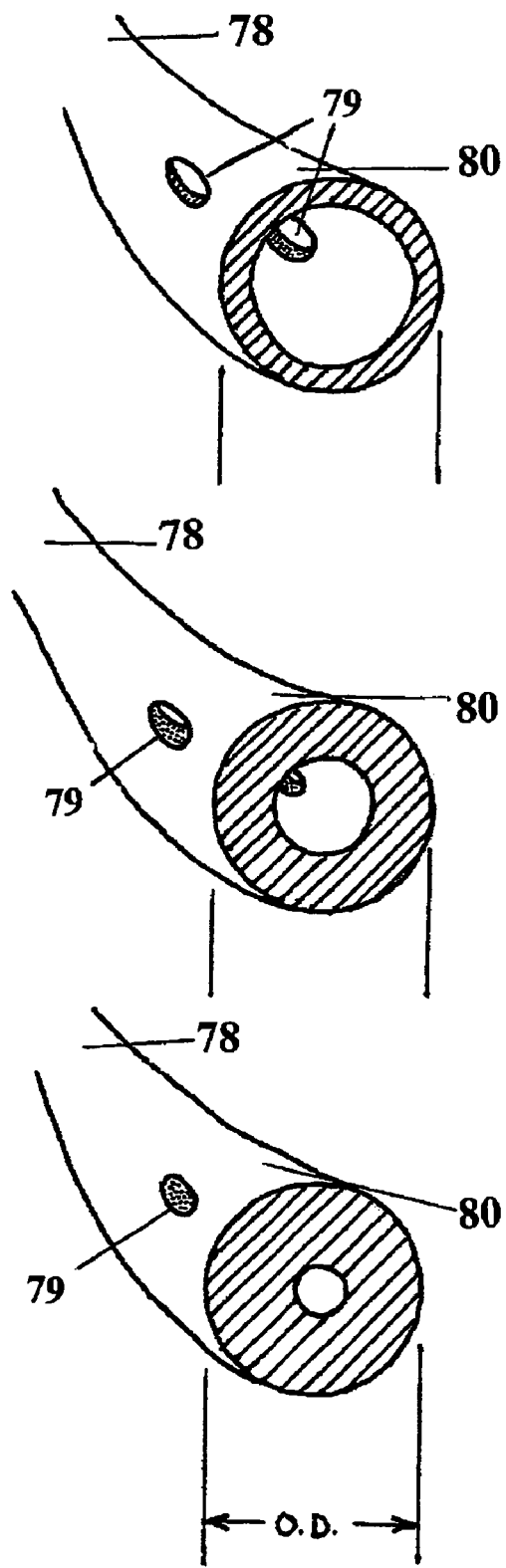
FIG. 5 is an illustration of tubes with different wall thickness which can be selected for use according to a first embodiment of the invention.

Referring to FIG. 5 a tube adapted to be engaged by the dilator of the first embodiment is depicted. The tube 78 may be an elongate cylindrical member shaped to include a trailing end (not shown) and a leading end 80. The leading end 80 is adapted to be engaged by the protrusions 18, 46 of the first and second portion of the dilator 12, 38. Preferably the end of the tube 80 will have one or more indents 79 to engage the protrusions 18, 46. In FIG. 5 the indents are in the form of two apertures through which the protrusions 18 and 46 may be received. The leading end of the tube 80 may alternatively be solid with a passage through which the protrusions 18 and 46 may pass.

Figure 6:
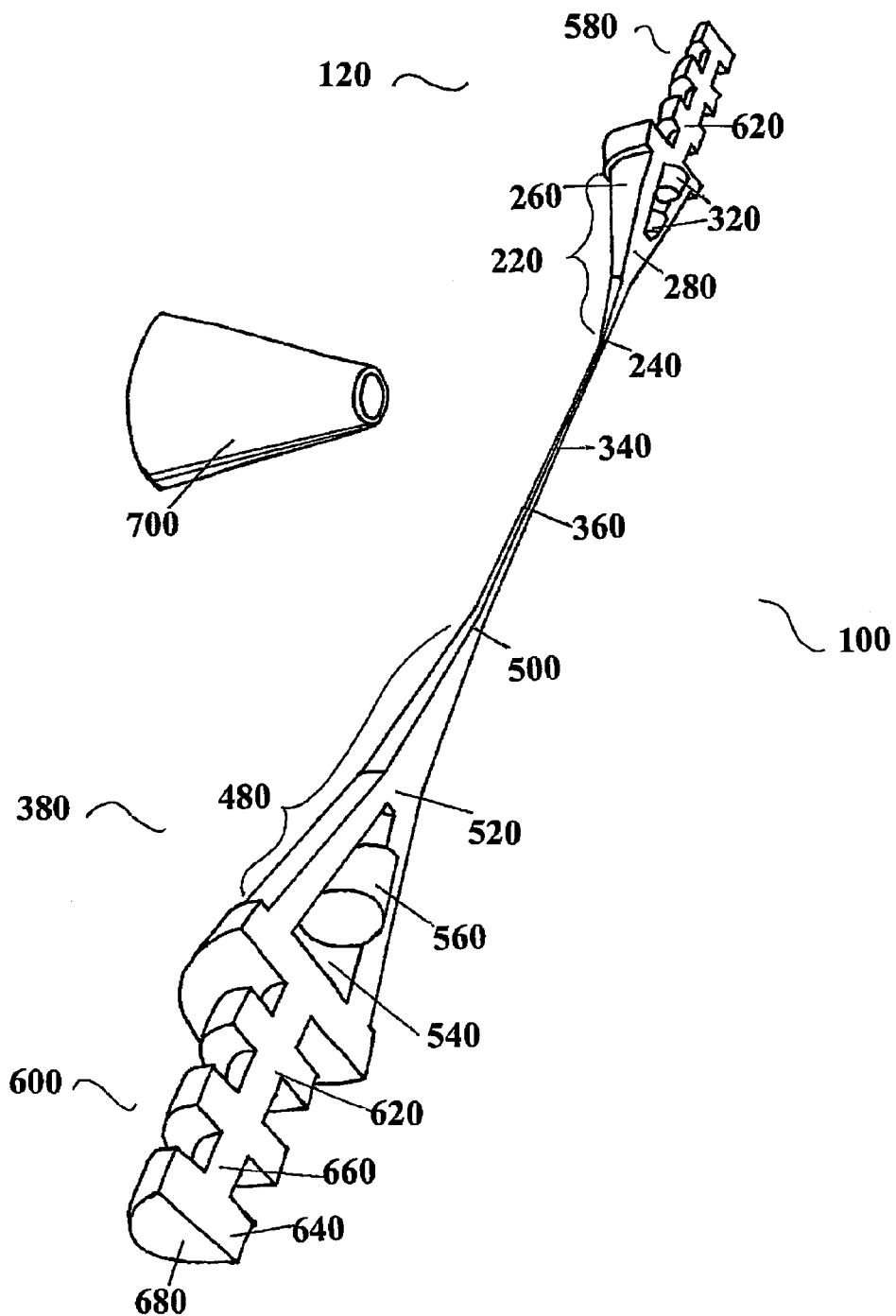
FIG. 6 is an illustration of a dilator before assembly according to a second embodiment of the invention.

Referring to FIG. 6 in accordance with a second embodiment a dilator is depicted, wherein like numerals define like parts in accordance to those described in the first embodiment. Instead of a lip 16, 42 described in the first embodiment the second embodiment has a flange 580 that protrudes from the end of the main portion 220 and a second flange 600 that protrudes from the second end of the second main portion 480. The first and second flange 580, 600 have a flat inner surface 620 with an elongate piece 640 extending from the predominantly flat outer segment 280, 520 of the main portion 220, 480 to an end. A rib segment 660 intersects the elongate piece 640 wherein the elongate piece 640 looks like a backbone with ribs extending across the elongate piece at several points. The rib segments 660 also extend transversely from the inner surface 620 to form a curved configuration in a semicircular shape that act as barbs 680 able to engage the leading end of the tube 80.

Referring to FIG. 2, and FIG. 6 in accordance with a first and second embodiment accordingly a dilator 10, 100 is formed from a suitable material having sufficient rigidity to open a stoma and sufficient flexibility to permit it to be bent through a patient. The dilator 10, 100 as shown in FIG. 2 and FIG. 6 may be made of a single suitable material. In the first and second embodiments polyethylene is used, however, other suitable polymers such as polypropylene or nylon or semi-rigid plastics known to those skilled in the art may be used. Therefore, the material can be manufactured in a single step using a suitable process such as injection molding, compression molding, transfer molding or other molding processes known in the art.

Figure 3:
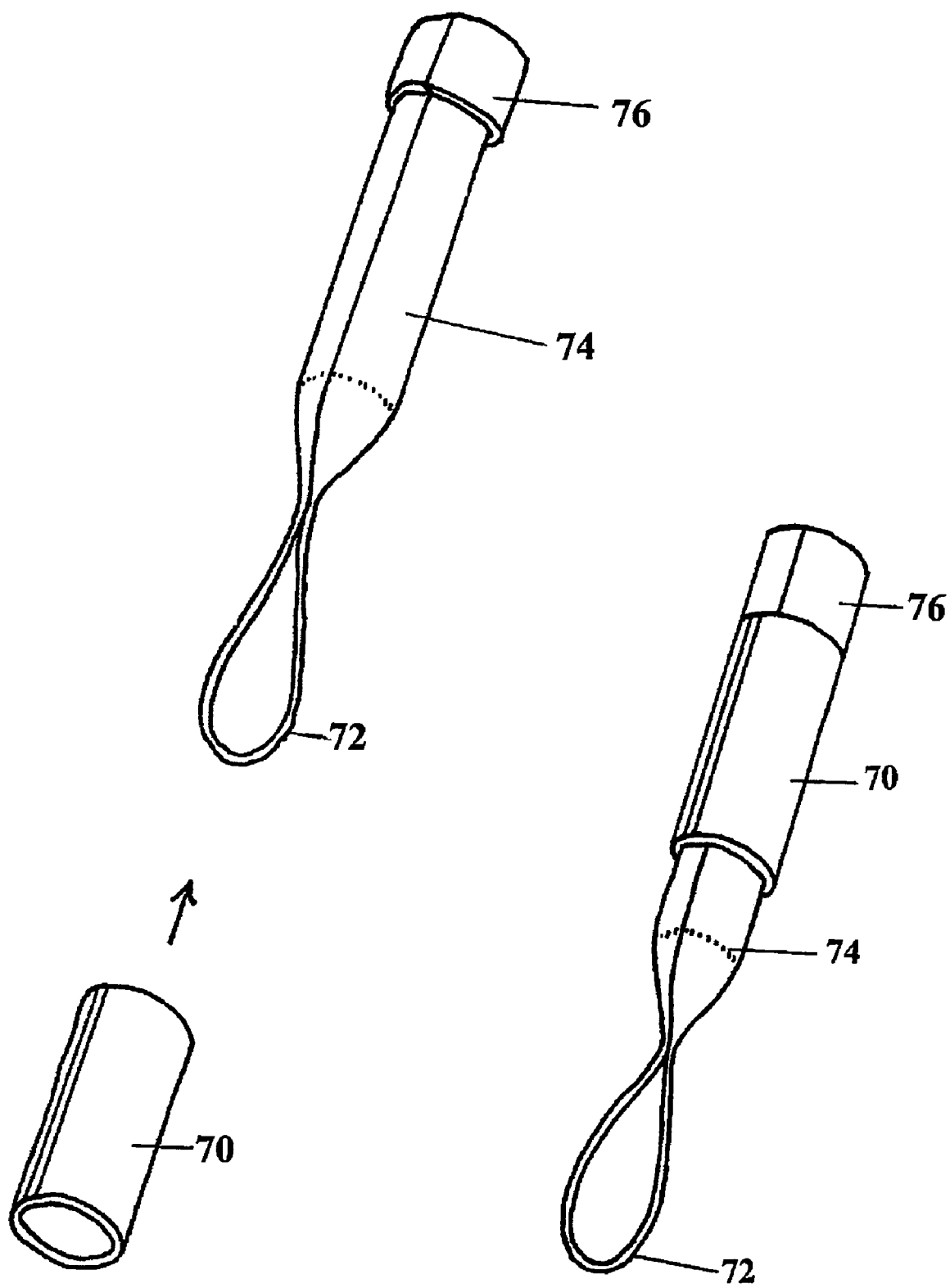
FIG. 3 is an illustration of an assembled dilator according to a first embodiment of the invention.
Figure 4:
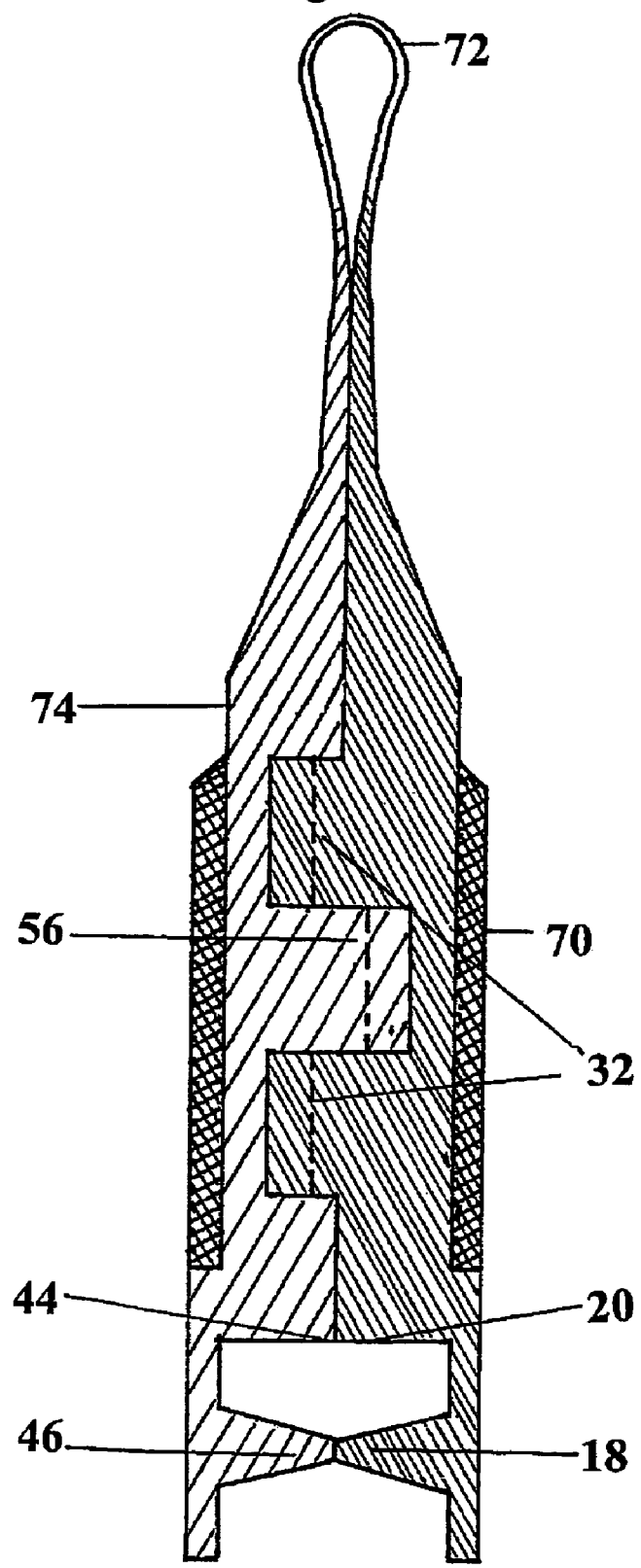
FIG. 4 is a longitudinal cross-sectional view of the assembled dilator according to a first embodiment of the invention.

A mold formed in the inverse of the dilator may be cast to form a dilator 10, 100. The first portion of the dilator 12, 120 connected to a second portion of the dilator 38, 380 by a central filament 34, 340 such that the first 12, 120 and second portion 38, 380, when coupled together, causes the central filament to fold back on itself and become a pull loop 72 as shown in FIGS. 3 and 4. When assembled the central filament serves as the pull loop 72 while the first 12, 120 and second portion 38, 380 serve as the two halves of the conical shaped dilator 74.

The projections 32, 320 of first main portion 22, 220 of the dilator enter the recesses within the second main portion 48, 480. Similarly the projection 56, 560 of second main portion 48, 480 of the dilator enter the recess within the first main portion 22, 220. The first and second main portions are pushed together until predominantly flat outer segment 28 and 52 of the first and second main portion are contacting each other. Such that when the first portion 12, 120 is connected to the second portion 38, 380 they couple nicely with the projections received in the recesses allowing the first and second portion to interlock as shown in FIG. 4.

An assembled conical shaped dilator 74 and pull loop 72 is formed when the dilator 10, 100 is folded and the first 12, 120 and second portion 38, 380 are coupled as mentioned above. As the dilator is pulled through the tissues, the tissues exert forces which tend to maintain the coupling and keep the first and second portions together, re-enforcing the coupling mechanism. When in use, the resultant forces actually compress the two halves together rather than tear them apart. In fact, there is no significant force which tends to separate the two halves. If required the complete conical shaped dilator 74 and pull loop 72 may be de-coupled by pulling them apart.

An embodiment may further include a hollow piece 70, 700 which can be slid over the complete conical shaped dilator 74 and pull loop 72 to surround the conical shaped dilator 74, further reducing any chance of separation. The hollow piece 70, 700 should be a suitable shape to allow it to slide over the pull loop 72 and onto the conical shaped dilator 74 to form a snug fit over the conical shaped dilator 74. For example the embodiment in FIGS. 2, and 3 has a cylindrical shaped hollow piece 70 whereas the embodiment in FIG. 6 has a frusto-conical shaped hollow piece 700. Alternatively the first and second portion can be self-locking by modifying the projections and recesses to contain catches in which case the hollow cylinder 70, 700 is optional. An alternative to the hollow piece would be to use a standard surgical suture to tie the first and second portion together, both portions having an appropriate groove on the surface of the dilator to accommodate the ligature.

In the first embodiment shown in FIG. 2 when the dilator 10 is assembled the first and second lip 16 and 42 form a sheath 76 and the cavities form a hollow indent surrounded by the sheath 76 adapted to envelope the leading end of the tube 80. The sheath 76 has an internal diameter larger than the external diameter of the leading end of the tube 80 such that it is adapted to envelope the end of the tube 80. By having sheath 76 envelope the leading end of the tube 80, this minimizes any possibility of snagging of tissues by the edge of the tube. Furthermore, the tunnel created in the tissue from pulling the assembly shown in FIG. 3 through said tissue will consequently have a larger diameter than the tube. Therefore, any frictional force on the tube is reduced.

The protrusions 18, 46 of the first embodiment shown in FIG. 2 may be in the form of pegs or teeth molded into the cavity at the first 14 or second end 40 of the first 12 and/or second portion 38 of the dilator. The protrusions 18, 46 being adapted to engage the leading end of the tube 80 either by gripping or passing into the tube adapted to be engaged by the protrusion 18, 46 of the dilator thereby connecting the leading end of the tube 80 to an end of a conical shaped dilator 74. This prevents de-coupling of the dilator from the end of the tube in use.

The protrusions 18, 46 may be teeth that firmly bite into a part or the full circumference of the tube. The engagement of the end of the tube 80 and the dilator 10 may be achieved by bonding.

The choice of engagement for the tube end 80 and the dilator 10 will depend on the physical and chemical properties of the material the leading end of the tube 80 is made of. The tube 78 may be made from a soft flexible medical-grade silicone or polymer (such as polypropylene, polyurethane or other material suitable for use as a gastrostomy tube) whereby the tube can form a loop without kinking, or narrowing of the internal diameter. The leading end of the tube 80 may be of the same material or may be constructed of a harder plastic or suitable material.

It can be easily appreciated that a tube with any wall thickness can be used with the first embodiment providing a great flexibility in the choice of tubes that can be used. FIG. 5 depicts tubes with three different internal diameters. All three tubes can be used with the first embodiment where the embodiment is the same made to the same specifications and dimensions.

A second embodiment of the single dilator and pull loop 100 is seen in FIG. 6 has a first and second flange 580, 600 rather than a first and second lip 16, 42 defining a cavity. When the first portion 120 is coupled to the second portion 380 the first and second flange 580, 600 form a plug preferably having barbs or ribs or other formations that will increase gripping within the tube when the plug is inserted into the leading end of a tube. The gripping is to ensure that the dilator and tube do not separate easily.

When the first flange 580 on the first portion of the dilator 120 is brought together with the second flange 600 of the second portion of the dilator 380 the plug is formed. The plug may then be plugged into the leading end of the tube and used in a similar manner to known dilators. Additionally, the hollow piece 700, if used, could be modified to envelope the edge of the tube, and/or to hold the tube firmly against the plug.

In one embodiment, the dilator 10, 100 and/or tube 78 is packed and delivered to doctors in a kit, unconnected in a ready to assemble form. The dilator can be easily assembled and the tube 78 can then be connected to the assembled dilator by the doctor or other medical personnel at the time of or prior to the gastrostomy procedure.

In another embodiment, the dilator 10, 100 and tube 78 are preassembled and connected as described herein, before packing in the kit and delivery.

Preferably the kit is packed in sterile conditions suitable for medical use.

The kit is easy for any medical personel to use whether it come preassembled or ready to assemble.

Various embodiments and extra features are envisioned in relation to the present invention. They include:
  The invention can be used in any surgical procedure requiring the placement of a medical catheter (whether for feeding, draining, anchoring, stenting constricting or a combination of functions) for example the invention may be used in traditional open surgery, laparoscopic surgery, thoracoscopic surgery, cystoscopy, colonoscopy, or trans-natural orifice surgery.
  The invention can be modified for use in veterinary surgery.
  The invention can be modified to serve as a trocar and cannula for use in minimally-invasive surgery.

Alternatively the central filament may be made from a material different from that of the first and second portion and may be embedded during the molding process The central filament may be molded separately having barbs at either end that may be snapped into receiving channels within the first and second main portion before the dilator is assembled.

The first portion and the second portion do not have to be precisely half of the assembled dilator provided they interlock to form the assembled dilator. In other embodiments one portion may be minimized to merely the features required to interlock that portion with the other portion to form a functioning dilator when assembled.

Modifications and variations as would be apparent to a skilled addressee are deemed to be within the scope of the present invention.

I claim:

1. A medical dilator for a gastrostomy feeding tube comprising a first portion, a second portion, and a central filament having a first end and a second end, wherein the first end of the central filament is connected to the first portion, and the second end of the central filament is connected to the second portion such that when the first and second portion are coupled together to form an assembled dilator, the central filament folds back on itself to form a pull loop; and the first portion of the dilator further comprises two or more projections interspaced with a recess between the projections, the second portion of the dilator comprises one or more projections between recesses such that, when the first and second portions are coupled, the projections on the first portion are received within the recesses of the second portion and vice-versa, the alternating arrangement interlocking to secure the coupling.

2. The dilator of claim 1, wherein the dilator consists of a polymer that has sufficient rigidity to open a stoma, yet flexible enough to allow the dilator to be bent through a patient.

3. The dilator of claim 1, further comprising a first and second lip that forms a sheath when the dilator is assembled the sheath adapted to envelope an end of the tube.

4. The dilator of claim 1, further comprising a first flange protruding from the first portion and a second flange protruding from the second portion, the first and second portion arranged to form a plug adapted to firmly engage the tube when the dilator is assembled.

5. The dilator of claim 4, wherein the plug comprises barbs to securely grip the internal diameter of the tube.

6. The dilator of claim 1, further comprising a hollow piece adapted to surround the assembled dilator.

7. The dilator of claim 6, wherein the hollow piece is cylindrical.

8. The dilator of claim 6, wherein the hollow piece is frusto-conical.

9. The dilator of claim 1, where the assembled dilator has a base and a top, the top being the portion from which the central filament extends to form a pull loop, the assembled dilator further comprising at least one protrusion extending from the base to engage an end of the tube.

10. A tube for gastrostomy feeding comprising one or more indents near an end thereof for facilitating connection of the tube to the dilator of claim 9 and engaging the protrusion of the dilator when the dilator is connected to that end of the tube.

11. A tube for gastrostomy feeding comprising one or more indents near an end thereof for facilitating connection of the tube to the dilator of claim 9, wherein the one or more indents further comprises one or more apertures for receiving the protrusions of the dilator of claim 4, when the dilator is connected to that end of the tube.

12. A kit comprising the dilator of claim 1, and a tube adapted to be engaged by the dilator.

13. The kit of claim 12, wherein the dilator is assembled.

14. A kit comprising the dilator of claim 9, wherein the assembled dilator is connected to a tube for gastrostomy feeding comprising one or more indents near an end thereof for facilitating connection of the tube to the dilator and engaging the protrusion of the dilator when the dilator is connected to that end of the tube.

* * * * *